United States Patent [19]

Grage, Jr.

[11] Patent Number: 5,082,626
[45] Date of Patent: Jan. 21, 1992

[54] WEDGE SHAPED TEST STRIP SYSTEM USEFUL IN ANALYZING TEST SAMPLES, SUCH AS WHOLE BLOOD

[75] Inventor: Henry M. Grage, Jr., Indianapolis, Ind.

[73] Assignee: Boehringer Mannheim GmbH, Mannheim, Fed. Rep. of Germany

[21] Appl. No.: 230,303

[22] Filed: Aug. 8, 1988

[51] Int. Cl.⁵ .................... G01N 1/18; G01N 33/48
[52] U.S. Cl. ........................ 422/56; 422/58; 436/165; 436/169
[58] Field of Search ............. 422/56, 58; 436/165, 436/169

[56] References Cited

U.S. PATENT DOCUMENTS

| | | | |
|---|---|---|---|
| 4,201,548 | 5/1980 | Tamaoku et al. | 422/58 |
| 4,254,083 | 5/1981 | Columbus | 422/58 |
| 4,582,684 | 4/1986 | Vogel et al. | 422/57 |
| 4,678,757 | 7/1987 | Rapkin et al. | 422/58 |
| 4,810,470 | 3/1989 | Burkhardt et al. | 422/58 |
| 4,826,759 | 5/1989 | Guire et al. | 422/58 |
| 4,826,772 | 5/1989 | Meathrel | 422/58 |
| 4,876,067 | 10/1989 | Deneke et al. | 422/58 |
| 4,910,150 | 3/1990 | Doeding et al. | 422/58 |

OTHER PUBLICATIONS

"Detection of Ambient Hydrogen Chloride with a Zinc-Coated Piezoelectric Crystal Resonator Operating in a Frequency-Time Differential Mode", G. Neuburger, Anal. Chem., vol. 61, pp. 1559-1563, Jul. 15, 1989.

*Primary Examiner*—Robert J. Warden
*Assistant Examiner*—Lyle A. Alexander
*Attorney, Agent, or Firm*—Felfe & Lynch

[57] ABSTRACT

An apparatus useful in analyzing samples, such as body fluids, is presented. The device is especially useful in analyzing whole blood because its configuration, with a differential vertical dimension permits rapid flow and uniform draw through the device, with contact of the relevant portion of the sample to a reagent means. Also disclosed is a method for analyzing a sample using the device.

27 Claims, 5 Drawing Sheets

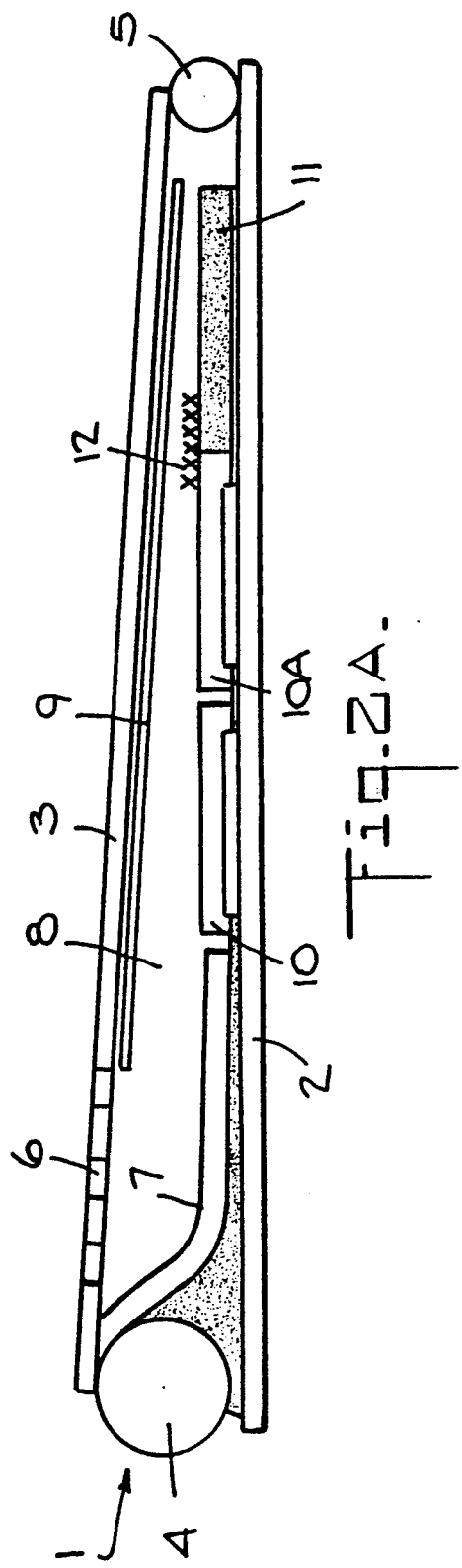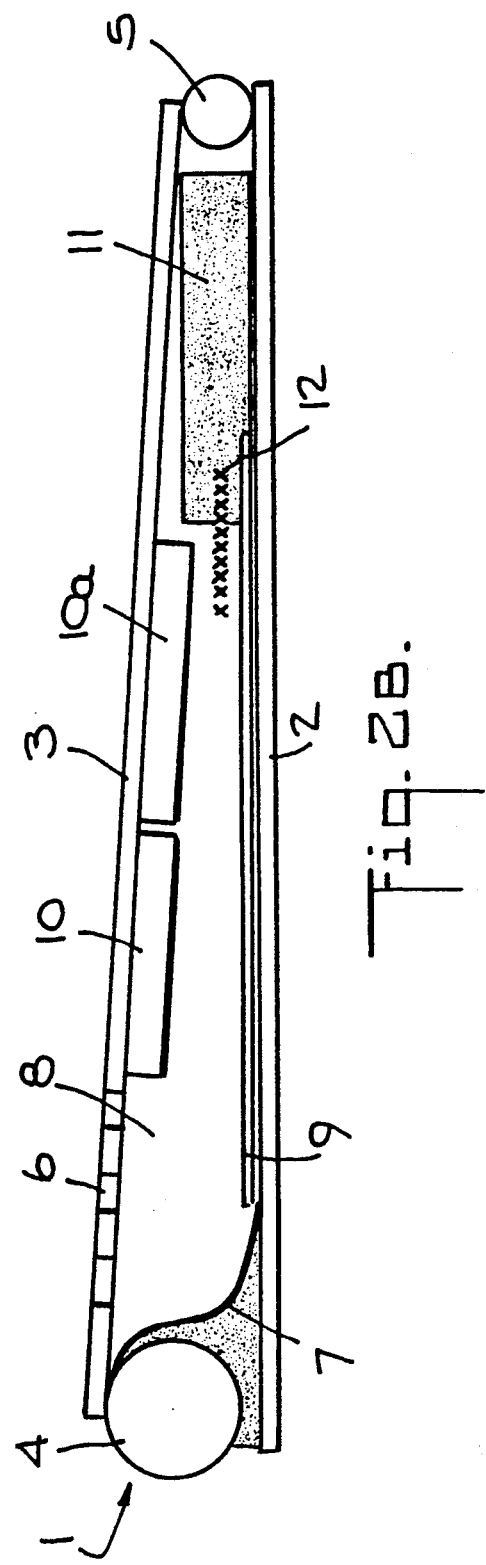

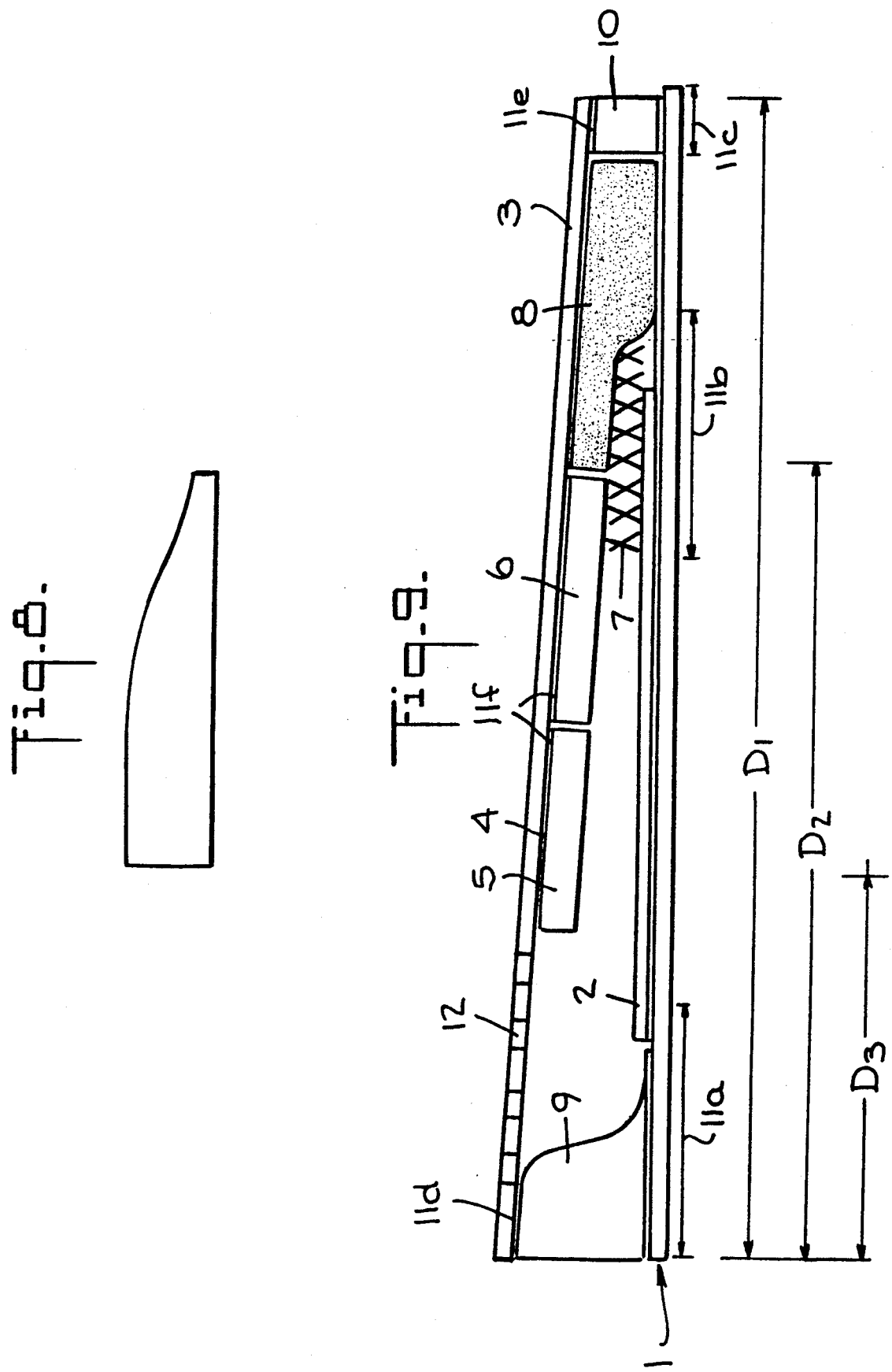

WEDGE SHAPED TEST STRIP SYSTEM USEFUL IN ANALYZING TEST SAMPLES, SUCH AS WHOLE BLOOD

FIELD OF THE INVENTION

This invention relates to the field of clinical chemistry. More particularly, it relates to apparatus used in analyzing fluid samples in order to determine an analyte or analytes contained therein. Of particular pertinence is the usefulness of the device in analyzing whole blood in situ, i.e., without the need for an earlier separation or filtration step, and an additional feature, which is the elimination of a cleaning or wiping step. As such, the apparatus will be referred to herein as a "non-wipe test strip", or "NWT".

BACKGROUND AND PRIOR ART

Clinical chemistry is a field concerned, inter alia, with the analysis of various substances to determine elements, or "analytes" thereof. Of particular importance in this field is the analysis of samples taken from humans in order to diagnose for diseases, to determine licit or illicit drug consumption and overdoses, and so forth. Generally, the analytical techniques employed to carry out these processes involve analyzing a sample of a body fluid, such as urine, blood, feces, and other biological exudates. Among the analytes determined in various analytical tests are glucose levels (in blood or urine); bilirubin (blood); hormones, such as human chorionic gonadotropin, or hCG (urine), which leads to diagnosis or monitoring of conditions such as diabetes. Measurement of hCG is a common way of determining whether a woman is or not pregnant. Opiates such as morphine and heroin, and toxins such as digoxin are also determined in standard analytical assays, as are essential ions, such as $Ca^{2+}$, and $K^+$. Examples of the art as applied to determination of specific analytes include Sena, et al., Clin. Chem. 34(3): 594 (1988) (creatinine); Hafkenscheid, et al., Clin. Chem. 34(1): 155-157 (1988) (gamma glutamyl-transferase, creatine kinase, etc.); U.S. Pat. No. 4,069,016 (bilirubin); U.S. Pat. No. 4,452,887 (glucose); Reissue 32,016 (lactic acid and lactase). These references are merely exemplary, as even the most cursory of reviews will produce many different assay methods for various analytes.

Assays for determining sample analytes can be divided into two major groups: homogeneous and heterogeneous assays. Of the two, it is the latter group to which this invention is directed, and the following discussion concerns this group.

A heterogeneous assay involves two phases: solid and liquid. The liquid phase contains the analyte to be determined, and the liquid is contacted to a solid phase, which has been pretreated to contain some substance which reacts with the analyte to be determined, producing some observable reaction.

The field contains innumerable examples of heterogeneous assays, and the observable reactions produced therein. Exemplary of these are U.S. Pat. No. 4,376,110, which describes so-called "sandwich" assays. In these assays, a sample is contacted to a solid phase containing an antibody to the analyte being determined. Binding occurs between the two, and then a second monoclonal antibody, containing a label is contacted to the bound complex. The label, which can be, e.g., an enzyme is then "read" by contacting it with a substrate, forming a detectable color. Measurement of the intensity of the color is a measure of how much analyte is bound to the solid phase. The color can be read visually, or by various photometric or spectrophotometric means, which are well known to the skilled artisan.

More typical of heterogeneous assays, however, are those described by e.g., U.S. Pat. No. 4,069,016 (Wu), cited supra. In this patent, the bilirubin assay involves contacting the sample to a solid phase, which contains various chemical substances which interact in the presence of bilirubin to produce a detectable shift in the color of the sample. This shift in color is read, as indicated supra, as an indication and measurement of bilirubin content. Also typical of such systems is U.S. Pat. No. 4,452,887, also cited supra. The device discussed therein is adapted for measuring glucose. In the device, referred to as a "dry type" apparatus, glucose is acted upon by glucose oxidase, forming a product which is in turn acted upon by other reactants, leading to the production of hydrogen peroxide. The hydrogen peroxide, in turn, reacts with an indicator such as a tetrazolium salt (e.g., 3,3',5,5' tetramethylbenzidine or "TMB"), or a different nitro- or phenyl type indicator, forming a color. One then observes or measures the color as an indication of the presence and/or amount of glucose. This serves as a means for diagnosing, e.g., *diabetes mellitus*, or to monitor blood sugar levels of a diabetic.

Various formats have been developed in the field for performing assays of the type described supra. One kind of strip, the "impregnated bibulous paper" type, is described, e.g., in U.S. Pat. Nos. 4,446,232; 4,235,604; and 4,459,358. All of these devices rely on the diffusion of liquid through an absorbent material, such as filter paper. If the liquid contains the analyte of interest, various reactions occur at reaction stations, or "zones" spaced throughout the device. The idea of reactions occurring at different points in the apparatus can also be a feature of the "layered" type of apparatus, represented, e.g., by U.S. Pat. Nos. 4,069,015; 3,992,158; 4,256;693; 3,901,657; and 4,144,306. In these devices, different layers are either connected, or are in fluid contact with each other such that clear demarcations can be seen in the different zones of the devices. These zones serve different functions, including evenly distributing the analyte containing sample for distribution through the device (a "spreading layer", e.g., in U.S. Pat. No. 3,992,158); and reagent zones, whose function is evident, as well as light impermeable layers. This feature serves to present a more easily readable signal after color formation takes place, because stray light does not interfere with the generated signal.

Yet another configuration of analytical test devices is the type which, physically, most represents the idea of a "test strip". These devices combine features of the layered device with those of the bibulous paper device, sand are represented, e.g., by U.S. Pat. Nos. 4,477,575, and 4,076,502. In these devices a sample is applied to a region of the strip which is configured in a layer fashion, and passes therethrough, and reaches a region which is configured in a fashion similar to bibulous paper strips. Frequently, in the first part of the device the sample undergoes preparatory steps, such as buffering or filtering, and undergoes chemical analysis in the second portion.

Yet another version of a test device has recently become available, the so-called "channel model" test strip. This type of device presents a sealed, canal shaped device through which sample flows, and is positioned with various reaction sites where sample analysis takes place. Attention is drawn to German patent specification DE 3 643 516 which corresponds to U.S. Pat. Application Ser. No. 134,950.

All of these devices can be used for analysis of some body fluids. A problem arises, however, with the analysis of whole blood, which requires special adaptation of the test device.

It will be recognized that whole blood has a distinct, dark red color. This property of blood makes it extremely difficult to analyze it in systems where color formation or change is involved, because the red color of the blood obscures or interferes with the indicator reaction going on.

In recognition of this problem, various test devices have been developed which do permit one to analyze whole blood. These devices usually include a feature which selectively filters erythrocytes from the sample, permitting passage of clear plasma into the actual testing region. Thus, U.S. Pat. No. 4,477,575 features a filtering membrane of glass fibers of particular dimensions. U.S. Pat. No. 4,256,693 suggests that filter paper can be used to remove the red blood cells, while U.S. Pat. No. 4,476,222 proposes coating a carrier with a mixture of polymethacrylate and polyvinyl formal. U.S. Pat. No. 4,594,327 incorporates a ligand receptor specifically chosen to bind to, and remove erythrocytes from the sample, while U.S. Pat. No. 4,478,944 teaches specific polymeric coatings which impede passage of erythrocytes into a testing region. Other test devices feature membrane filters (U.S. Pat. No. 3,663,374) or the use of carbohyrdate or amino acid molecules to remove the erythrocytes from the sample. See, e.g., U.S. Pat. Nos. 4,678,757 and 3,552,958. U.S. Pat. No. 4,543,338, also teaches such a device, where a test paper is coated with a partially cross-linked polymer. As this last patent's title attests, these are all "Wipe-off Test Devices", in that they require the investigator to wipe away the filtered erythrocytes from the test system.

As pointed out, the foregoing devices all require wiping off of the filtered red blood cells. This presents various problems both to the clinician and the layperson, from the viewpoint of accuracy, convenience and of safety. Blood samples can often contain infectious agents or toxins which present a hazard to the individual analyzing the sample. One contemporary example of this human immunodeficiency virus (HIV), which is known to be transmissible via the blood. It is of course desirable to alleviate or eliminate the problem of putting the investigator into contact with the blood sample.

From the standpoint of accuracy, test devices are extremely sensitive and delicate equipment. As such, elimination of as much intervention as possible is a desired goal. Finally, in terms of convenience, it will be understood that while the layperson might perform a single test per day in, e.g., home monitoring of glucose levels, the laboratory clinician may routinely perform hundreds of such tests in a day. The "wiping-off" which may take only a few seconds or a minute for one test, is magnified by the sheer number of tests which must be carried out in a given time period.

It will be seen, then, that one is confronted with an apparently resolvable problem. If one the one hand, the red blood cells are not removed from a sample, analytical sensitivity is impaired. If, on the other hand, the red blood cells are removed, other problems arise. Separating the red blood cells from the sample by, e.g., centrifugation prior to analysis, is not an option for the home tester, and presents problems such as erythrocyte lysis, etc., in the laboratory.

A key advance in the field was presented by the so-called "channel model" device disclosed in German Patent Specification 36 43 516, corresponding to U.S. Ser. No. 134,950, of which the present inventor is a co-inventor.

It was realized in the course of development of test devices for analyzing whole blood that there were three areas of major concern. The device had to facilitate flow of blood therein, enable it to be drawn out, and had to show complete removal of the blood sample. All three criteria had to be satisfied in order to achieve any meaningful improvement.

The "channel model", referred to supra, accomplished this to some extent. Its structure allows for improved blood flow into the capillary space it provides, and achieves rapid withdrawal or drainage. This model, however, did not always solve the problem of complete withdrawal. Unless an airtight seal is achieved in the channel model, when blood flows in, air is drawn in as well. Air creates "bubbles", which break up the continuous stream of blood in the device. The result is that blood further along the device than the air bubble is removed, but with the break in continuity, the blood behind the bubble is not. The sample becomes discontinuous, and blood backs up in the device.

Additionally, the channel model construction requires an amount of sample which is rather large and inconvenient, especially in "user friendly" or "at home" type tests. In these, the consumer/user must prick a finger, e.g., and hold it to the device until sufficient blood is taken up for analysis.

It is an object of this invention to present an apparatus useful in determining an analyte in a fluid sample, such as whole blood, which is not subject to the above identified problems, which requires less sample than other available devices, which can carry out analyses more quickly than other available systems, and which delivers blood to a reaction area quickly, followed by rapid removal.

It is a further object of of the invention to provide a method for analyzing a fluid sample for an analyte using the aforementioned device.

How these and other objects of the invention are achieved will be seen from review of the disclosure which follows.

SUMMARY OF THE INVENTION

It has now been found that an apparatus suitable for determining an analyte in a fluid sample can be provided which addresses and eliminates the problems described supra. A key feature of the device is the provision of a hollow space therein, which possesses a vertical dimension at one end which is greater than the vertical dimension at the other.

BRIEF DESCRIPTION OF THE FIGURES

FIGS. 2a and 2b show side views of two preferred embodiments of the invention: one with matrix exposed reagent pads (MER) (i.e. 2a); and one with surface exposed reagent pads (SER) (2b).

FIG. 8 shows a one piece construction of joining means and carrier means produced by, e.g., extrusion processes.

FIG. 9 refers to example 1, and shows a preferred embodiment of the device.

DETAILED DESCRIPTION OF PREFERRED EMBODIMENTS

Figure 1A:
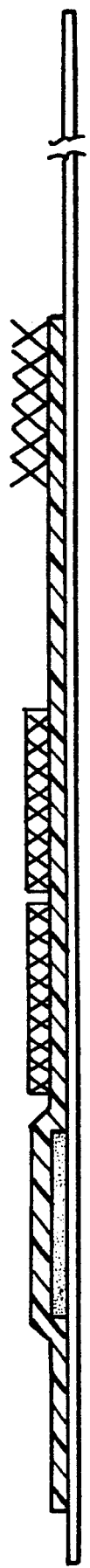
FIG. 1 labeled "Prior Art", depicts the channel model described in Ser. No. 134,950.
Figure 1B:
Figure 1C:
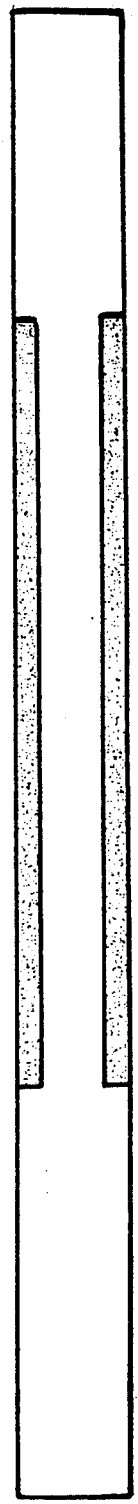
Figure 3:
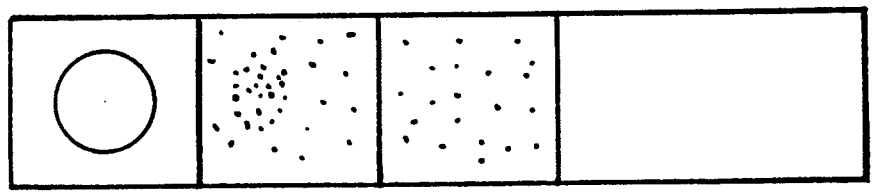
FIG. 3 is a top view of an embodiment of the invention.
Figure 4:
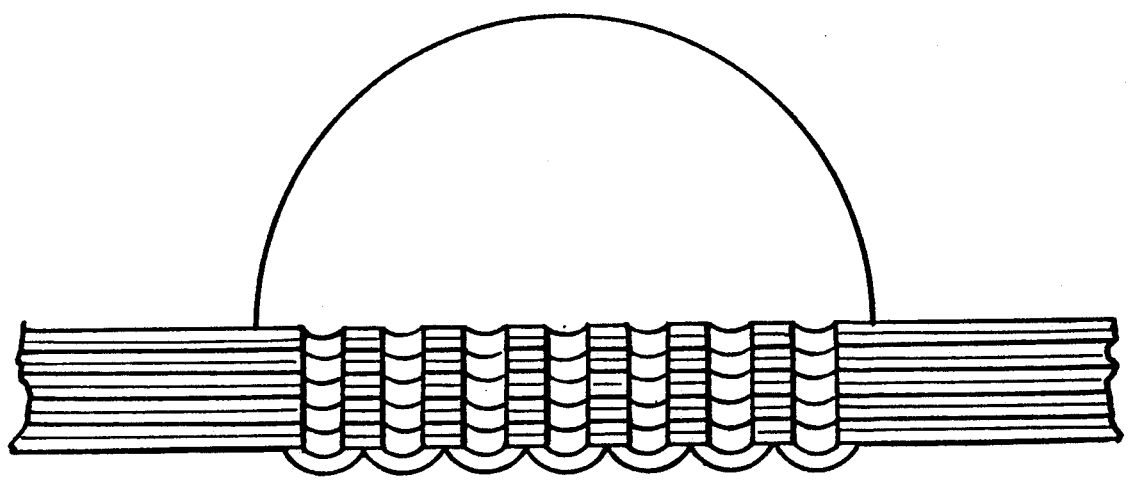
FIG. 4 is a close up, side cut away view of an embodiment of the sample port of the invention.

The invention is a device or apparatus for use in determining an analyte in a sample. The device comprises a carrier means and a covering means, which are joined together at two ends. In being joined together, the device is configured so that, at one end, the vertical dimension produced by joining the carrier and covering means is greater than that produced by joining carrier and covering means at the second end. These first and second ends will be referred to as the "beginning" and "end" portions of the device, so as to distinguish them from the two side portions of the device.

No discussion is provided herein as to the sealing of the side portions of the device, because they are not sealed. It has been found that the strong capillarity and draw produced by the device prevents fluid sample from escaping through the unsealed sides, even though escape of fluid might be expected to be a problem.

The configuration described results in formation of a hollow space between said carrier and covering means which itself possesses a greater vertical dimension at one end then the other.

Referring now to FIGS. 2a and 2b, one will see embodiment of the device described herein, which contains optional or alternate features as well as essential features. Alternate and optional features will be indicated in the description which follows.

With reference to FIG. 2, a device 1 in accordance with the invention is depicted. The apparatus depicts a carrier means 2 and a covering means 3 which are joined together by optional joining means 4 and 5. The joining means are optional because the device may be configured so that the carrier means 2 and covering means 3 are either joined together directly, or are joined by a means which does not display an actual physical structure. For example, when the device is prepared, e.g., by extrusion processes or by lamination, there will be no joining means presented. Further, the carrier and covering means may be joined by glue, hot melted materials, tape, or other means which are not adequately represented by 4 and 5.

The covering means 3 presents a port 6, through which sample is introduced. The covering means is configured out of any of a number of materials suitable therefor. Included within the scope of possible materials for the covering means are plastics, polymers, foils, films, mylar, and so forth. The only necessary criterion for the selection of covering means is that it not be dissolvable in the sample. The same options are available for the carrier means.

The port 6, of course, is provided to introduce the sample. Optionally, the port means can be treated with a material which increases the flowability of the sample introduced therethrough, i.e., renders it more hydrophilic. Example of such materials include various anionic, cationic, and nonionic surfactants. Many materials may be so used, which will be clear to the skilled artisan. Further elaboration is found infra.

In some situations, a test device following this invention is used where the portion containing the reaction zone is introduced to a device adapted for "reading" the reaction between a blood component, such as glucose, and a reagent. As this portion is in the reading device, sample application is made possible by extending the device. In this embodiment, the covering means and carrying means are still joined at two ends, but, rather than a structure where the vertical distance between one end and the other continually decreases, the device is configured so that, over at least a portion of the length between the two ends, the distance between covering means and carrier means is constant, i.e., they are parallel to each other. At some point along the length between the ends, the vertical distance begins to decrease. In this embodiment, the sample port is positioned in the covering means along the portion which is parallel to the carrier means.

Also pictured in FIG. 2 is fluid transport facilitation means 7, which facilitates the flow of sample through the device. This "ramp means" permits the flow of sample into the capillary or hollow space. The slope of this fluid transport facilitation means may act to increase the rate of flow of sample into the capillary space. The choice of material for construction of the ramp means may vary, and substances to increase flowability may also be impregnated, incorporated, or coated herein as well.

It will be seen from the figure that hollow space 8 has a varying, or sloping vertical dimension, which is a result of the configuration of the joined edges of the carrier and covering means at different vertical dimensions.

Hollow space 8 contains capillary means 9, which is involved in passing the sample through the device. As shown, capillary means 9 appears as a thin layer of film. This is one option. Others include treated paper, fabric, fibers, and so forth, which facilitate movement of the sample.

The structures 10 and 10a represent a plurality of reagent means in the device, although only a single reagent means is required. These take the form, in the depicted embodiment, of reagent pads containing ingredients which react with a component of the sample to give a detectable signal. It is important to note that the reagent means need not be configured on the covering means, and may be positioned, e.g., on the carrier means. Just as the placement of the reagent means can vary, so, too, can its "reading configuration". It is to be understood that test apparatus can be read either via the use of a reflection spectrometer or other device, or via the naked eye.

Figure 5:
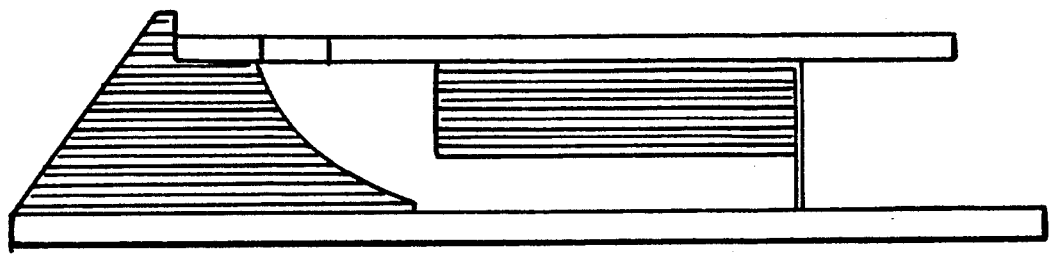
FIG. 5 is a partial side view emphasizing an embodiment of the fluid transport facilitating means.
Figure 6:
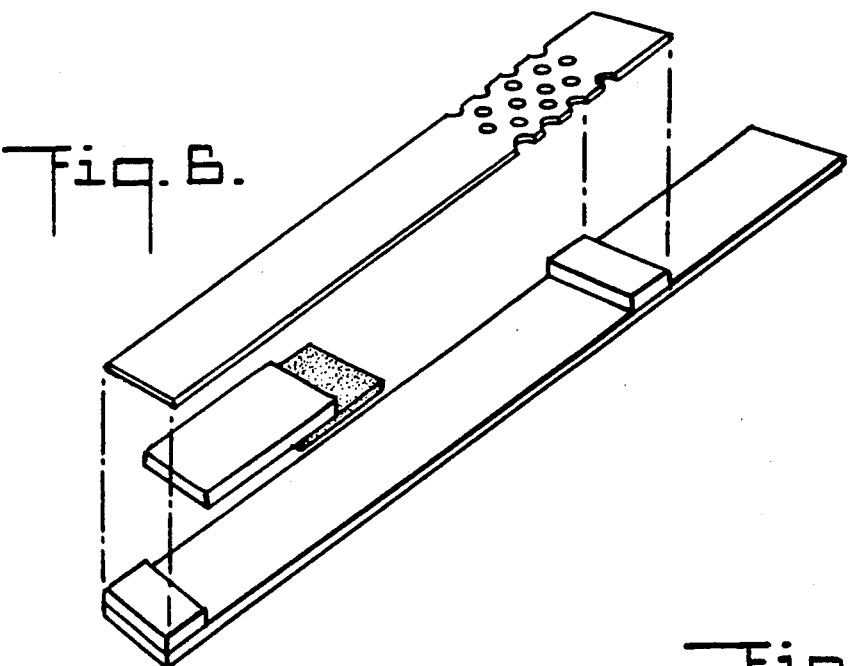
FIG. 6 is an exploded perspective of all embodiment of the invention.
Figure 7A:
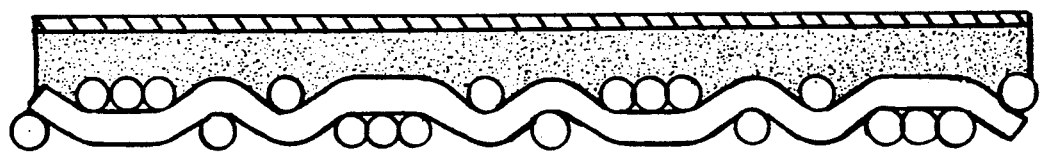
FIG. 7a-b shows side views of a "matrix exposed reaction" (MER) pad, and a "surface exposed reaction" (SER) pad.
Figure 7B:
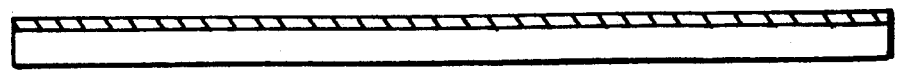

Various embodiments of the device are possible. One particularly preferred embodiment uses what is referred to herein as the "profile" means. The foregoing discussion has shown that the fluid transport facilitation means begins at the point where the first ends of the covering and carrier means are joined. When a joining means is used, or when the fluid transport facilitation means is joined directly to either the covering or carrier means, the "ramp profile", as depicted in FIG. 5 may be used. This embodiment is preferred because its shape improves the efficiency of the device, reduces the amount of sample necessary, and because the shape is easy to produce by various means, including extrusion processes.

The ramp profile means, it will be understood, is not the only way in which the covering means and carrier means can be joined together. The carrier means, for example, may be constructed as a "roofless" trapezoid, such as is depicted in FIG. 8. Extrusion processes are particularly well suited for preparing this type of carrier means. When this type of carrier means is used, the covering means is joined directly to the carrier means. Other embodiments employ joining means which are separate structures from the carrier and covering means. Among the type of joining means envisioned for the device described herein are stacked, double stick tape, and non-compressible plugs of, e.g., monofilament, plastic, polymer, or other materials. These "plugs" may be cylindrical, cubic, etc., and may be solid or hollow. While it is advantageous and most practical to use two joining means which are of the same shape, this is not essential. It is, of course necessary when joining means are used that the joining means connecting the first end of the carrier and covering means have a greater vertical dimension (i.e., be taller), than the second joining means. These joining means may be a permanent fixture of the device, such as in a device produced using an extrusion process, or may be removable.

When chemical joining means are used, such as glues, hot melts, lamination means, etc., the same parameters apply, i.e., the first joining means is greater in its vertical dimension than the second joining means.

The joining of the carrier and covering means at two ends with a height differential produces an angled, hollow space. The first end of the device, i.e., the higher end, is where a sample application port is positioned in the covering means.

The device has a fluid transport facilitating means positioned in the hollow space formed by the joined cover and carrier means. This fluid facilitating means may be a part of the first joining means, creating the ramp profile referred to supra, or it may be as simple as a hydrophilic surfaced foil, positioned between the joining means and the covering means. The fluid facilitating means, as is seen in FIG. 2 (ref. numeral 7), forms an angle with the cover means. The measure of the angle formed thereby may vary, but the preferred measure of the so-called wedge angle is $1.10° \pm 0.50°$.

The hydrophilic nature of the fluid transport facilitating means, whether in ramp profile form or otherwise, enables the sample to flow into the rest of the hollow space, i.e., the capillary space. When in the capillary space, the fluid moves over the reagent means, such as the SER or MER pads, resulting in the reaction of the reagent with the analyte to be detected. The reagent means is positioned in the hollow space, either on the cover means or the carrier means, but always between the fluid transport facilitating means and the absorption means.

It is possible to use a test device employing a single reagent means, such as one SER or one MER pad. More frequently, however, it is desirable to use more than one reagent means. When this embodiment is used, a problem emerges in that flow can be interrupted by the junction between the two reagent means. It has been found that this problem can be avoided by decreasing the depth of capillary space provided to the fluid, i.e., by ensuring that the second reagent means extends further into the capillary space than the first. By "second" is meant the reagent means closer to the second end of the device.

This difference in height, or "step" can vary, although it is preferred that the height differential be at least 33 um. Especially preferred are differentials of from about 40 um to 75 um, and a differential of 50 to 63 um in optimal.

When multiple reagent means are used, it is essential that these be configured so that liquid sample be able to move from one means to the other. This can be accomplished by various means well known to the art, such as by configuring the device so that the contact angle between sample and carrier means created by interaction of these two and the reagent means increases from the first reagent means to the next. Making the second reagent means larger than its predecessor is one way of accomplishing this.

The absorption means 11, positioned between the reagent means and the second end of the device, can consist simply of material capable of absorbing the excess fluid sample, or can include a mesh means 12 for facilitating the transition from the open capillary space to the absorption or draining means.

The invention will be seen to be an apparatus useful in analysis of a fluid sample. The apparatus comprises a carrier means and a covering means joined to each other at two ends. At one of the ends, the cover means is equipped with a sample application port, and this end has a vertical dimension greater than the vertical dimension of the second end. This joined structure results in the formation of a hollow space between the carrier and cover means. A fluid transport facilitating means is positioned at the first end, and extends into the hollow space but terminates before the second end. Also positioned in the hollow space at a point after the termination of the fluid transport facilitating means but before the second end is a reagent means adapted for measurement or determination of a particular analyte. Finally, positioned after the reagent means but before the second end is an absorption means adapted for absorption of whatever fluid is not absorbed by the reagent means.

The materials which are used to construct the various elements of the device and thus the device itself are those which are well known to the skilled artisan. The carrier and cover foils, for example, should be materials which do not dissolve in the fluid being analyzed. Examples of appropriate substances include polystyrene foils, mylar films, and so forth. Thickness of the materials is not particular critical within the normal ranges in the field. Typically, the cover and carrying means will be, e.g., 350–500 um thick.

In use, it is desirable that the sample application port on the cover means can be treated with a hydrophilic agent so that when samples enter the hollow space they are more hydrophilic than when not treated. An especially preferred mode of treatment involves treating the sample application port with a detergent solution, such as a solution of DONS (sodium di-octyl sulfyl succinate), ranging, e.g., from 0.1 to 10%. The treatment takes the form of applying the detergent solution to any or all of the top surface of the cover means, the internal space of the port, and the bottom surface of the cover. It has been found, using means well known in the art, such as by measuring solution contact angle, that the best results occur when all of the aforementioned surfaces are so treated. Alternatively, it may be desirable to treat the fluid sample prior to addition to the device to render it hydrophilic. Such treatment has no bearing on the device itself. The diameter of the port can vary: a preferred embodiment has the diameter ranging from 1 to 4 mm. By "port" is meant the means by which the fluid enters the capillary. It is not limited to a single opening, as the port may consist, e.g., of a sieve like array of smaller openings, or one larger one.

Moving to the elements within the hollow or capillary space itself, the fluid transport facilitating means is also hydrophilic. The hydrophilicity can be a result of the inherent properties of the material making up the element, or by treating the element, such as with a hydrophilic detergent.

The fluid transport facilitating means may be made of a material having the same hydrophility as the reagent means, but this is not essential. In preferred embodiments, hydrophilic foils and films such as polyester films, are chosen. Using techniques known to the art, and as alluded to, supra, it has been found that, optimally, the fluid transport facilitating means is chosen to produce a contact angle between fluid and surface of less than 45°, although the device will operate at angles greater than this.

Turning to the reagent means, at least one of these is required in the apparatus, but more than one are appropriate in many situations. In a particular preferred embodiment, reagent means are chosen which yield a contact angle from about 40 to about 50 degrees with a test fluid. When the reagent means is in the form, e.g., of an SER or MER pad, the means can range from 25 to 200 um in height in preferred embodiments. The pads, or reagents means, can be made of any of the standard hydrophilic materials used in analytical elements, such as fleeces of cotton, cellulose, rayon or mixtures thereof; hydrophilic polymers films; and mixtures of these materials. The reagent means, of course, contain agents which react with an analyte to form a detectable signal. Among the possible elements of the reagent means include enzymes such as glucose oxidase, peroxidases, alkaline phosphatases, and so forth. Indicator substances, such as tetramethylbenzidine, MBTH, MBTHS, ortho-anisidine, nitrophenylated amyloses etc., can all be included. Thus, by choice of appropriate reagent means or systems, one can measure analytes such as glucose, hormones such as hCG and LH, enzymes such as pancreatic alpha amylase, cholesterol, HDL, LDL, VLDL, creatinine amidinohydrolase, pathogens, including human immuno- deficiency virus (HIV), chlamydia, hepatitis virus; toxins such as digoxin; drugs such as marijuana, LSD, and so forth. The choice of what material is included in the reagent means is limited only by what substances are available which react with the analyte in question to produce a determinable signal.

The absorption means, or sink, can be provided either alone, or in combination with a hydrophilic mesh means. The material used to construct the absorption means should be sufficiently absorptive to pick up all excess sample, which is not in fact, very much. Many materials inherently possess this property, such as cottons, cellulose, rayon, polyethylene films, polypropylene films and mixtures of the foregoing. Even normally hydrophobic materials, such as glass fiber meshes, can be used if treated so as to become hydrophilic by, e.g., treatment with detergents like DONS, polyethylene glycol, ICONOC, and so forth. Cotton fibers, however, are preferred. Similarly, non-woven materials, such as those composed of synthetic fibres, unpolymerised fibreglass, and glass fibers, can be used.

When a mesh means is used to facilitate transport of fluid into the absorption means, it, too, must be hydrophilic or must be treated to become hydrophilic, using any of the means to accomplish this referred to supra. The choice of mesh means is not dictated by either the thickness, the size of the pores, or the percent open area. Mesh means ranging from 50 to over 300 um in thickness, with pores from 30 um up through 355 um, and with anywhere from 20% to 55% open area have all been used successfully. In an especially preferred embodiment, a mesh of 280 um in thickness, with pores or 280 um, is used.

In the apparatus described herein, the relative placement of the individual elements is not a critical feature of the device. It has been found, however, that a particularly preferred embodiment results when a particular distance between the carrier means and the reagent means is established. In terms of the other elements of the device, if "H1" is the measure of the greater vertical dimension of the two edges and "H2" the smaller of these, "D" is the distance between the first end and the reagent means where the horizontal value "G" is to be used, "D1" is the distance between joined first end and joined second end, "T1" is the vertical dimension of the covering means plus anything attached thereto and "T2" the vertical dimension of the carrier means and anything attached thereto, then "G" the distance between carrier means and reagent means is chosen so that:

$$G = H1 - D/D1 \, (H1 - H2) - (T1 + T2).$$

Example 1

The following example shows one possible embodiment of the device described herein. It is not intended to be read as limitative of the general description of the device.

Referring to FIG. 9 a carrier film "1" of clear polycarbonate (380 um thick; 60 mm wide; 300 mm long) has applied thereto double stick tape 100 um thick. The adhesive tape is applied at various points so as to secure different components of the device. For example, a first adhesive tape "11a" is applied to secure the ramp means, is 9 mm wide and 270 mm long. A second adhesive "11b" of the same dimensions as the first, secures the mesh means to the carrier foil while a third "11c" secures a "foot" as joining means at the end of the sink. This adhesive section is 3 mm wide, and is also 270 mm long. A fourth adhesive "11d" secures the ramp to the covering means, and is 3 mm wide and 250 mm long, while a fifth adhesive "11e" (3 mm × 250 mm) secures the foot to the covering means. Finally, a sixth adhesive means "11f", in two parts, secures reagent pads to the covering means.

Following application of the adhesive to the covering means, a ramp means "9", made of polyvinylchloride and 270 mm long, is applied to the carrier foil. The transport film "2", of clear polyester and 180 um thick, 15 mm wide and 300 mm long is then applied to the carrier foil. The mesh means "7", 280 um thick, 8 mm wide and 250 mm long is then applied. This mesh means is polyester monofilament. The sink "8", which is constructed of a nonwoven absorbent material and the foot "10", made of polyvinyl chloride are then applied. The sink is 1 mm thick, 10 mm wide and 250 mm long, while the foot is 270 mm long.

Following the application of the materials described, supra, reagents means "5" and "6" which are respectively 150 um×5 mm×250 mm and 200 um×7 mm×250 mm in their dimensions and are made of white polycarbonate are applied to a cover film of white polystyrene 500 um×33 mm×250 mm in dimension. A spacer means "4" of white polystyrene 520 um×12 mm×250 mm separates these from direct contact of the cover means.

The above components are laid down and then cut into individual 5 mm strips. It will be understood that, if the components are laid down on the carrier in what is thought of as a "north-south" orientation, the cut is made going "east-west".

Some of the materials can be treated prior to assembly, as described supra. Thus, the ramp "9", the transport film "2", and the mesh "7", have all been treated to be made hydrophilic or more hydrophilic. Similarly, the cover means have holes "2" punched therethrough, which holes are also treated to be hydrophilic. Finally, the reagent means "5" and "6" are both treated to contain reagents in, e.g., the form of a film.

Referring to the formula described earlier, the following values are:
$H1 = 278$ um
$H2 = 2172$ um
$G1 = 556$ um
$G2 = 280$ um
with a ramp height of 1648 um, and a "foot" height of 1092 um. The angle formed is 1.08°, i.e., the angle between the ramp and the covering means at the point of contact therebetween.

In practice, blood is drawn from the patient or user via standard means. The blood can be applied either via the application holes in the covering means or, if desired, to one of the open sides of the device. When the covering means is used as a delivery port, a sample of about 25 ul is required. When the application is to an open side, 15 ul or so is taken up automatically.

Blood flows rapidly into the space in less than 1 second. The sample fills and penetrates the flow regulation means in about 10 seconds. Drainage occurs progressively over about an additional 20 seconds, giving a total time in the chamber of about 30 seconds.

Following drainage, the only fluid remaining in the device is that which has penetrated the reagent means. This reagent means gives a detectable signal, such as color development which results from the reaction of a blood component, such as glucose, with reagents contained therein, such as glucose oxidase, peroxidase, and a tetrazolium salt. The color development is analyzed via means well known in the art (e.g., comparison to controls).

It will be appreciated that this optimization is only one possible embodiment of the invention. Different values for the height and length of the various components are possible, and are intended to be encompassed within the scope of the invention.

I claim:

1. Apparatus for analysis of a fluid sample, comprising:
   a carrier means and a covering means, each of which has two end portions and two sides between said two end portions, wherein a portion of said carrier means and said covering means are joined and a second portion of said carrier means and said covering means are joined to form a hollow space between said covering means and said carrier means, wherein said joined first portions have a greater vertical dimension than said joined second portions so as to form a wedge shape thereby, said covering means having a sample application port positioned thereon, a fluid transport facilitating means positioned in said hollow space beginning at said first end and terminating before said second end, at least one reagent means positioned between said fluid transport facilitation means and said second end, and a fluid absorption means positioned between said at least one reagent means and said second end wherein there is hollow space even when the reagent means, fluid transport facilitating means and absorption means are positioned in the apparatus.

2. Apparatus of claim 1, wherein said joining means for said first end portion and said fluid transport facilitation means form a one piece construction.

3. Apparatus of claim 1, wherein said reagent means is a surface exposed reagent means.

4. Apparatus of claim 1, wherein said reagent means is a matrix exposed reagent means.

5. Apparatus of claim 1, wherein said reagent means is positioned on said covering means.

6. Apparatus of claim 1, wherein said reagent means is positioned on said carrier means.

7. Apparatus of claim 1, further comprising a flow regulating means positioned in said hollow space.

8. Apparatus of claim 1, further comprising a mesh means positioned in said hollow space and extending from at least a part of said reagent means and into said absorption means.

9. Apparatus of claim 1, wherein said carrier means and said reagent means are separated by a distance G defined by:

$$G = H1 - D/D1\ (H1 - H2) - (T1 + T2)$$

wherein H1 is the vertical dimension of said joined first ends, D is the distance between said first end and said reagent means at which horizontal point the value of G is desired, D1 is the distance between joined first and second ends, H2 is the vertical dimensions of said second end, T1 is the vertical dimension of said covering means, and T2 is the vertical dimension of said carrier means.

10. Apparatus of claim 1, wherein said port is treated with a surfactant.

11. Apparatus of claim 1, wherein said covering means and said carrier means are arranged parallel to each other for a portion of their length between said two end portions and are not parallel for the remaining portion between said two end portions.

12. Apparatus of claim 11, wherein said sample port is positioned in said parallel portion of said covering means.

13. Apparatus of claim 1, wherein said absorption means is in fluid contact with said reagent means.

14. Apparatus of claim 13, wherein said flow regulating means is positioned on said carrier means.

15. Method for determining an analyte in a sample comprising contacting said sample to the apparatus of claim 1 and determining a detectable signal with said reagent means as an indication of said analyte.

16. Method of claim 15, wherein said sample is whole blood.

17. Apparatus of claim 1, wherein said first and second ends are joined by joining means.

18. Apparatus of claim 17, wherein said joining removable means are removable.

19. Apparatus of claim 17, wherein said joining means are solid.

20. Apparatus of claim 17, wherein said joining means are hollow.

21. Apparatus of claim 17, wherein said joining means are cylindrical or rectangular.

22. Apparatus of claim 17, wherein said joining means comprise monofilament.

23. Apparatus of claim 17, wherein said joining means comprise double stick tape, hot melt, or glue.

24. Apparatus of claim 17, wherein said carrier means, first joining means and second joining means form a one piece construction.

25. Apparatus of claim 17, wherein said covering means and said joined first portion form an angle of from 0.6 to 1.6 degrees relative to said covering means and said joined second portion.

26. Apparatus of claim 17, wherein said carrier means, first joining means, fluid transport facilitation means and second joining means form a one piece construction.

27. Apparatus of claim 26, wherein said one piece construction is produced by extrusion processes.

* * * * *